United States Patent
Lynch et al.

(10) Patent No.: US 9,856,221 B2
(45) Date of Patent: Jan. 2, 2018

(54) SALT OF IVABRADINE AND PROCESS FOR THE PREPARATION THEREOF

(71) Applicant: LES LABORATOIRES SERVIER, Suresnes (FR)

(72) Inventors: Michael Lynch, Saint Jean de la Ruelle (FR); Patrick Cointepas, Saint Jean de la Ruelle (FR); David Lafargue, Saint Jean le Blanc (FR); Gilles Briault, Saint Peravy Epreux (FR)

(73) Assignee: LES LABORATOIRES SERVIER, Suresnex (FR)

( * ) Notice: Subject to any disclaimer, the term of this patent is extended or adjusted under 35 U.S.C. 154(b) by 0 days.

(21) Appl. No.: 15/308,439

(22) PCT Filed: May 6, 2015

(86) PCT No.: PCT/FR2015/051201
§ 371 (c)(1),
(2) Date: Nov. 2, 2016

(87) PCT Pub. No.: WO2015/170053
PCT Pub. Date: Nov. 12, 2015

(65) Prior Publication Data
US 2017/0050932 A1   Feb. 23, 2017

(30) Foreign Application Priority Data
May 6, 2014  (FR) ..................... 14 54081

(51) Int. Cl.
C07D 223/16  (2006.01)
C07C 65/11   (2006.01)

(52) U.S. Cl.
CPC ............ *C07D 223/16* (2013.01); *C07C 65/11* (2013.01)

(58) Field of Classification Search
CPC .................................... C07D 223/16
See application file for complete search history.

(56) References Cited

U.S. PATENT DOCUMENTS 5,296,482 A   3/1994   Vian

FOREIGN PATENT DOCUMENTS

| EP | 0534859 A1 | 9/1992 |
|---|---|---|
| WO | WO 2011/104723 | 9/2011 |
| WO | WO 2011/157720 | 12/2011 |

OTHER PUBLICATIONS

International Search Report for PCT/FR2015/051201 dated Jul. 1, 2015.
Ferrari et al., European Heart Journal Supplements, 2005, 7 (Supplement H), H16-H21.
http://www.ema.europa.eu, Summary of Product Characteristics for Procolaran, Aug. 8, 2016.
https://www.drugs.com/pro/corlanor.html, Apr. 2015.

*Primary Examiner* — Bruck Kifle
(74) *Attorney, Agent, or Firm* — Hueschen and Sage

(57) ABSTRACT

Ivabradine hemipamoate of formula (I):

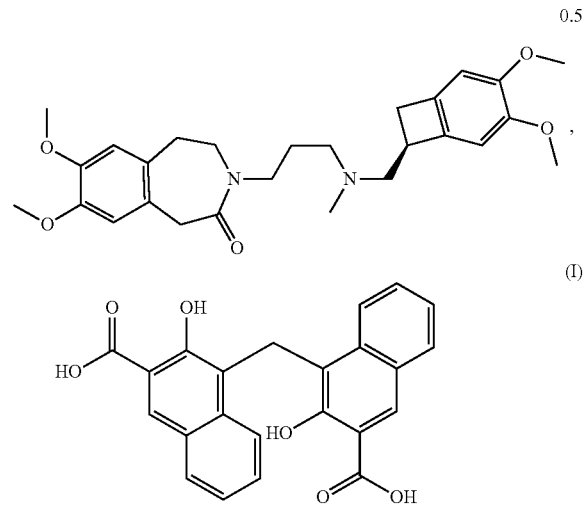

and its hydrates.
Medicinal products containing the same which are useful in the treatment or prevention of the various clinical situations of myocardial ischaemia such as angina pectoris, myocardial infarction and the associated rhythm disturbances, as well as in the various pathologies involving rhythm disturbances, especially supraventricular rhythm disturbances, and in systolic or diastolic heart failure.

6 Claims, 1 Drawing Sheet

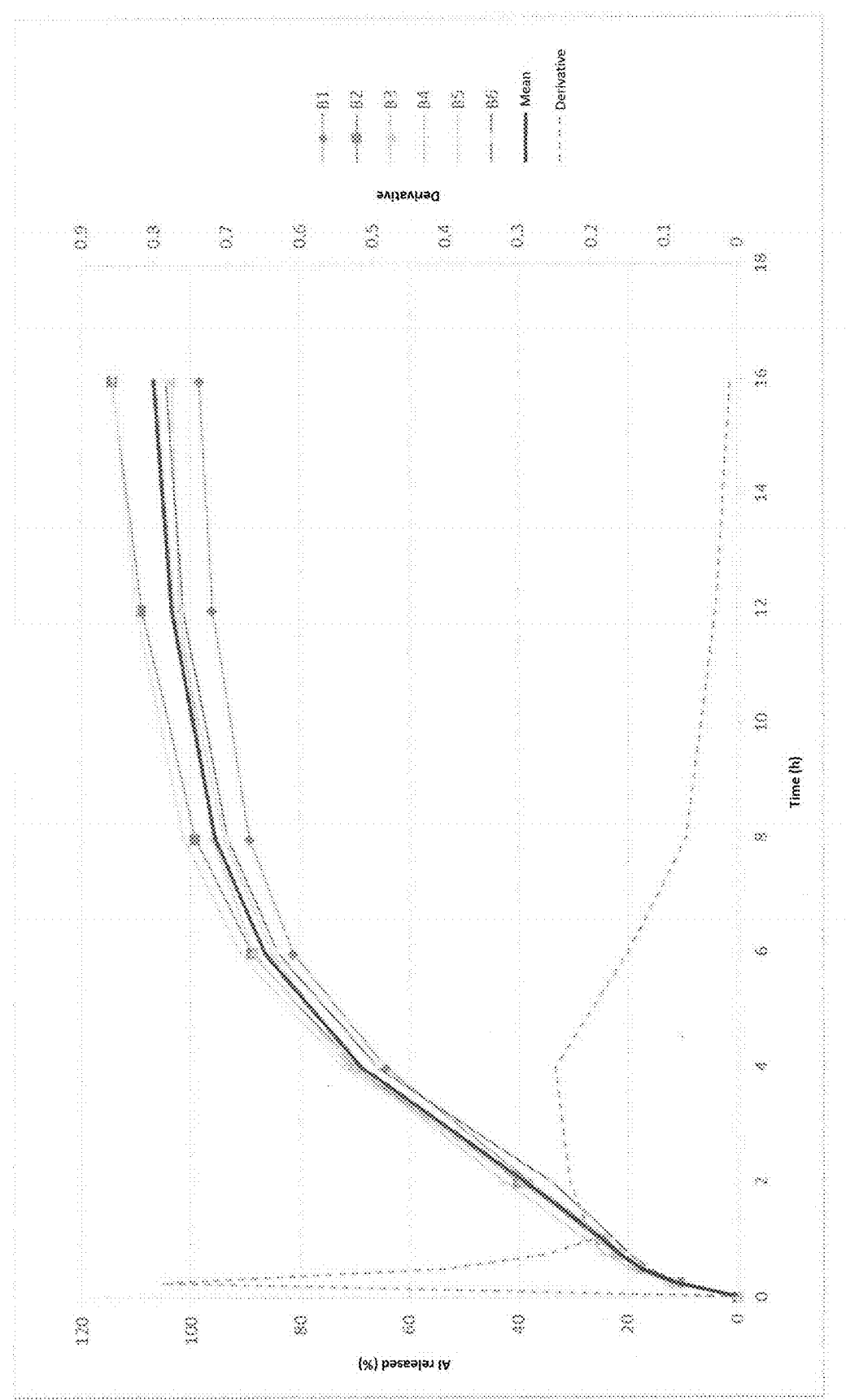

SALT OF IVABRADINE AND PROCESS FOR THE PREPARATION THEREOF

The present invention relates to a new salt of ivabradine, to a process for the preparation thereof, and to pharmaceutical compositions containing it.

Ivabradine, or 3-{3-[{[(7S)-3,4-dimethoxybicyclo[4.2.0] octa-1,3,5-trien-7-yl]methyl}-(methyl)amino]propyl}-7,8-dimethoxy-1,3,4,5-tetrahydro-2H-3-benzazepin-2-one, and its addition salts with a pharmaceutically acceptable acid, and more especially its hydrochloride, have very valuable pharmacological and therapeutic properties, especially bradycardic properties, which make these compounds useful in the treatment or prevention of the various clinical situations of myocardial ischaemia, such as angina pectoris, myocardial infarction and the associated rhythm disturbances, as well as in the various pathologies involving rhythm disturbances, especially supraventricular rhythm disturbances, and in heart failure, both systolic and diastolic.

The preparation and therapeutic use of ivabradine and its addition salts with a pharmaceutically acceptable acid, and more especially its hydrochloride, have been described in European patent EP 0 534 859.

The present invention relates to ivabradine hemipamoate of formula (I):

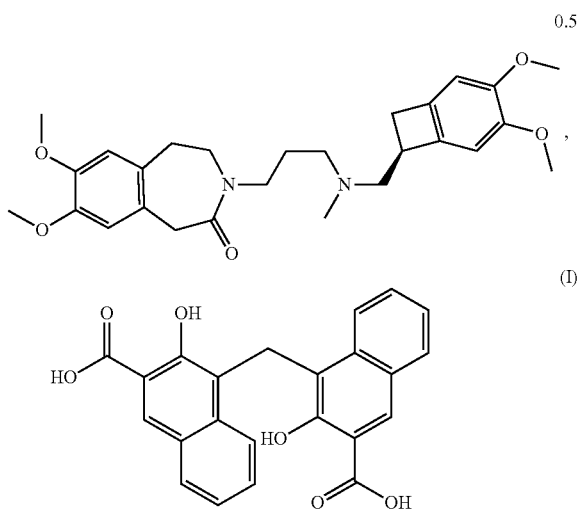

and its hydrates, to a process for the preparation of said salt, and to pharmaceutical compositions containing it, in particular those which permit controlled release of the active ingredient over time.

Pamoic acid is also called 4,4'-methanediylbis(3-hydroxynaphthalene-2-carboxylic) acid.

The compound of formula (I) has an ivabradine/pamoic acid ratio of 1/0.5.

The compound of formula (I) is obtained by treating ivabradine hydrochloride with the disodium salt of pamoic acid or sodium pamoate in an aqueous medium.

Ivabradine hydrochloride and sodium pamoate are brought together in a proportion of from 1/0.5 to 1/0.6.

The compound of formula (I) so prepared is then extracted from the aqueous medium by means of an organic solvent, for example dichloromethane.

After it has been formed, the compound of formula (I) can advantageously be taken up in methanol in order to remove the residual organic solvent.

The present invention relates also to pharmaceutical compositions comprising as active ingredient ivabradine hemipamoate, in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration and especially tablets, dragées, sublingual tablets, gelatin capsules, capsules, suppositories, creams, ointments, dermal gels, injectable or drinkable preparations, aerosols, eye or nasal drops.

In addition to ivabradine hemipamoate, the pharmaceutical compositions according to the invention comprise one or more excipients or carriers such as diluents, lubricants, binders, disintegrators, absorbents, colourings, sweeteners.

Examples of excipients or carriers which may be mentioned include:
for the diluents: lactose, dextrose, sucrose, mannitol, sorbitol, cellulose, glycerin;
for the lubricants: silica, talc, stearic acid and its magnesium and calcium salts, polyethylene glycol;
for the binders: aluminium and magnesium silicate, starch, maltodextrin, gelatin, tragacanth, methylcellulose, sodium carboxymethylcellulose and polyvinylpyrrolidone;
for the disintegrators: agar, alginic acid and its sodium salt, effervescent mixtures.

The percentage of ivabradine hemipamoate in the pharmaceutical composition is preferably from 5% to 50% by weight.

The dosage used varies according to the sex, age and weight of the patient, the administration route, the nature of the disorder and of any associated treatments and ranges from 2.5 to 30 mg of ivabradine per 24 hours, and more preferably from 5 to 15 mg per day, and yet more preferably from 10 to 15 mg per day.

The percentage of diluents in the pharmaceutical composition is preferably from 40% to 80% by weight.

The percentage of lubricants in the pharmaceutical composition is preferably from 0.2% to 10% by weight.

The percentage of binders in the pharmaceutical composition is preferably from 5% to 50% by weight.

The applicant has found that the use of ivabradine hemipamoate made it possible to prepare a pharmaceutical composition with controlled release of the active ingredient, while overcoming the problems generated by the conventional methods.

Numerous pharmaceutical compositions intended for the controlled release of pharmaceutical active ingredients have been proposed and produced, for their administration by the oral, buccal, sublingual, ocular, rectal, vaginal and/or parenteral route. The objectives of these new compositions were substantially as follows:
to reduce the frequency of administration of the medicaments,
to obtain relatively constant levels of active ingredient in the medium or at the intended biological site,
to obtain release profiles which are correlate with the pharmacological activity of the medicaments.

The principle that is most commonly used to control the release is to incorporate the active ingredient or ingredients with excipients, mostly of polymeric nature, in matrices.

Irrespective of the matrix compositions that are envisaged, the obtainment thereof encounters specific manufacturing problems such as:
complex manufacturing process in a plurality of steps,
stability of the active ingredient during the manufacturing process and with respect to the excipients used,
  modulation of the speed of release of the active ingredient or ingredients is difficult, often variable over time and dependent, for example, on the particle size of the batches of polymers with the compression methods,
  manufacturing process allowing a pharmaceutical form to be obtained that is substantially suitable for only one administration route,
  reproducibility of the batches owing to the multiplication of the steps.

The use of ivabradine hemipamoate makes it possible to obtain a controlled release profile of the active ingredient without employing the complex galenic formulation techniques described in the prior art.

Accordingly, the applicant has shown that the use of ivabradine hemipamoate in the pharmaceutical composition of the invention permits controlled release of ivabradine even when the galenic formulation used corresponds to that employed with ivabradine hydrochloride for the immediate release of the active ingredient.

While all the ivabradine hydrochloride is released in 15 minutes in vitro, the in vitro dissolution test described in the present application has shown that only 80% of the ivabradine hemipamoate had been released after approximately 6 hours.

The examples which follow illustrate the invention.

EXAMPLE 1

Preparation of Ivabradine Hemipamoate

The elemental analysis was performed on a Carlo Erba 1108 device.

The results are corrected by the water content of the product, which is 1.82% (measured by coulometry).

4.1 g of ivabradine hydrochloride (8.12 mmol) are dissolved in 200 mL of water, and 2.0 g of sodium pamoate (4.63 mmol) are dissolved in 200 mL of water.

The sodium pamoate solution is added to the ivabradine hydrochloride solution with vigorous stirring. The hemipamoate salt is formed immediately by precipitation. Stirring is maintained for about 30 minutes, and then the ivabradine hemipamoate is extracted once with 200 mL of dichloromethane and then a second time with 100 mL of dichloromethane. The organic fractions are combined and rinsed with 100 mL of water. The organic phase is dried with magnesium sulfate, yielding a clear yellow-coloured solution.

The organic phase is evaporated to dryness at 40° C. in vacuo in a rotary evaporator. A yellow powder is obtained.

The yellow powder is dried at 40° C. in vacuo (10 mbar) for 16 hours and then taken up in 200 mL of methanol.

The solution is evaporated to dryness at 40° C. in vacuo in a rotary evaporator. A yellow powder is again obtained.

The yellow powder is dried at 40° C. in vacuo (10 mbar) for 20 hours.

The $^1$H NMR spectrum shows a residual methanol content of 0.8%.

Subsequent drying of the powder at 80° C. in vacuo (10 mbar) for 24 hours yields 3.53 g of a product having a residual methanol content of less than 0.1%.

Yield=66.5%

Elemental Analysis:

| Element | % theoretical | % corrected mean |
|---|---|---|
| C | 69.77 | 69.40 |
| H | 6.69 | 6.60 |
| N | 4.23 | 4.25 |
| O | 19.31 | |

Method for Correcting the Results:
  Example for C: 69.14*100/(100−1.82)=69.40%
  Example for H: 6.68*100/(100−1.82)−2*1.82/18=6.60% (because the hydrogen atoms of water must be taken into account (2/18))

EXAMPLE 2

Pharmaceutical Composition

Preparation Formula for Tablets Containing a Dose of 5 mg of Ivabradine in 100 mg

| | |
|---|---|
| Ivabradine hemipamoate | 7.07 mg |
| Lactose monohydrate | 62.23 mg |
| Maize starch | 20 mg |
| Maltodextrin (Lycatab ® DSH) | 10 mg |
| Magnesium stearate | 0.5 mg |
| Anhydrous colloidal silica (Aerosil 200) | 0.2 mg |

EXAMPLE 3

Dissolution Test

Operating Conditions for Dissolution
  Paddle dissolution apparatus described in the European pharmacopoeia (2.9.3)
  Dissolution medium: 0.01 N hydrochloric acid (pH~2.1) degassed
  Temperature of the medium: 37° C.±0.5° C.
  Volume of the medium: 500 mL±5 mL
  Speed of rotation of the blades: 50 rpm±2 rpm
  Standard sampling time: 0, 15, 30 and 45 min
  Added sampling times: 1, 2, 4, 6, 8, 12 and 16 h
  Volume removed: 1 mL
  Replacement of the volume removed: no
  Number of units tested: 6
  Number of units per flask: 1

TABLE 1

Dissolution results

| Time (hour) | % of active ingredient released | | | | | | | Standard | |
| | B1 | B2 | B3 | B4 | B5 | B6 | Mean | deviation | Derivative |
|---|---|---|---|---|---|---|---|---|---|
| 0 | 0 | 0 | 0 | 0 | 0 | 0 | 0 | 0 | 0 |
| 0.25 | 12 | 11 | 12 | 13 | 12 | 11 | 12 | 0.84 | 0.79 |
| 0.5 | 18 | 17 | 18 | 20 | 17 | 16 | 18 | 1.15 | 0.4 |

TABLE 1-continued

| | Dissolution results | | | | | | | | |
|---|---|---|---|---|---|---|---|---|---|
| | % of active ingredient released | | | | | | | Standard | |
| Time (hour) | B1 | B2 | B3 | B4 | B5 | B6 | Mean | deviation | Derivative |
| 0.75 | 21 | 22 | 22 | 24 | 21 | 20 | 22 | 1.5 | 0.26 |
| 1 | 24 | 25 | 26 | 28 | 23 | 23 | 25 | 1.8 | 0.2 |
| 2 | 38 | 40 | 40 | 43 | 38 | 34 | 39 | 2.87 | 0.23 |
| 4 | 64 | 70 | 71 | 70 | 72 | 66 | 69 | 3 | 0.25 |
| 6 | 81 | 89 | 88 | 85 | 91 | 84 | 86 | 3.58 | 0.15 |
| 8 | 89 | 99 | 96 | 94 | 101 | 93 | 95 | 4.34 | 0.07 |
| 12 | 96 | 109 | 102 | 103 | 110 | 101 | 104 | 5.16 | 0.03 |
| 16 | 98 | 114 | 104 | 106 | 114 | 105 | 107 | 6.27 | 0.01 |

FIG. 1 is a graphical illustration of the data presented in the table above.

The invention claimed is:

1. Ivabradine hemipamoate of formula (I):

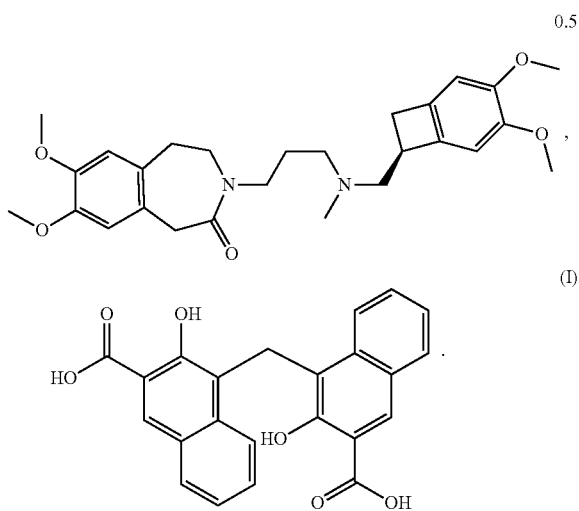

(I)

2. A process for the preparation of ivabradine hemipamoate according to claim 1, wherein ivabradine hydrochloride is brought together with sodium pamoate in an aqueous medium in a proportion ivabradine hydrochloride/sodium pamoate of from 1/0.5 to 1/0.6, to form ivabradine hemipamoate of formula (I), which ivabradine hemipamoate is then extracted from the aqueous medium by means of an organic solvent, followed by removal of the solvent under vacuum, to yield ivabradine hemipamoate.

3. A pharmaceutical composition comprising as active ingredient ivabradine hemipamoate according to claim 1, in combination with one or more inert, non-toxic, pharmaceutically acceptable excipients or carriers.

4. A method of treating a condition selected from the group consisting of clinical situations of myocardial ischaemia; pathologies involving rhythm disturbances; and systolic or diastolic heart failure, in a subject in need thereof, comprising administration of an effective amount of ivabradine hemipamoate according to claim 1, alone or in combination with one or more inert, non-toxic, pharmaceutically acceptable excipients or carriers.

5. The method of claim 4, wherein the condition is selected from the group consisting of angina pectoris and myocardial infarction and the associated rhythm disturbances.

6. The method of claim 4, wherein the condition is a pathology involving supraventricular rhythm disturbances.

* * * * *